United States Patent
Parekh et al.

(10) Patent No.: US 6,326,026 B1
(45) Date of Patent: *Dec. 4, 2001

(54) SUBCOATED SIMULATED CAPSULE-LIKE MEDICAMENT

(75) Inventors: Kishor B. Parekh, Horsham; Dennis C. Wieand, Coopersburg; Jean B. Leasure, Penllyn, all of PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,173

(22) Filed: Jan. 14, 2000

Related U.S. Application Data

(60) Division of application No. 09/389,793, filed on Sep. 3, 1999, now Pat. No. 6,214,350, which is a division of application No. 09/292,211, filed on Apr. 15, 1999, now Pat. No. 6,120,801, which is a division of application No. 08/802,185, filed on Feb. 18, 1997, now Pat. No. 5,916,592, which is a continuation of application No. 07/784,623, filed on Oct. 31, 1991, now Pat. No. 5,658,589, which is a continuation-in-part of application No. 07/345,599, filed on Apr. 28, 1989, now abandoned.

(51) Int. Cl.$^7$ .................................................. A61K 9/48
(52) U.S. Cl. ...................... 424/463; 424/451; 424/453; 424/456; 424/464; 424/474
(58) Field of Search ................................. 424/463, 456, 424/451, 453

(56) References Cited

U.S. PATENT DOCUMENTS

| | | |
|---|---|---|
| 540,538 | 6/1895 | Colton . |
| 599,865 | 3/1898 | Richards . |
| 724,436 | 4/1903 | Clark . |
| 1,115,426 | 10/1914 | Green . |
| 1,377,644 | 5/1921 | Warrington . |
| 2,370,698 | 3/1945 | Vaughn . |
| 2,373,721 | 4/1945 | Taylor et al. . |
| 2,847,809 | 8/1958 | Lindeman et al. . |
| 3,045,641 | 7/1962 | Oddo . |
| 3,141,792 | 7/1964 | Lachman et al. ........................ 118/6 |
| 3,185,626 | 5/1965 | Baker .................................. 424/479 |
| 3,453,989 | 7/1969 | Bippus ................................. 118/503 |
| 3,538,997 | 11/1970 | Catasauqua ......................... 198/131 |

(List continued on next page.)

FOREIGN PATENT DOCUMENTS

| | | |
|---|---|---|
| 1217140 | 1/1987 | (CA) . |
| 1223209 | 6/1987 | (CA) . |
| 127081 | 10/1928 | (CH) . |
| 24 34 803 A1 | 2/1975 | (DE) ............................. A21C/9/04 |
| 0 023 327 | 1/1981 | (EP) . |

(List continued on next page.)

OTHER PUBLICATIONS

Physician's Desk Reference, Product Identification, PDR 32 Edition, 1978, p. 438.

Physician's Desk Reference, Product Information, PDR 32 Edition, 1978, pp. 1754–1755; 1760–1761; 1806–1807; and 1808–1809.

Porter, Stuart C., "Coating of Pharmaceutical Dosage Forms", Remington's Pharmaceutical Sciences, Chapt. 91, pp. 1633–1643, 17th Edition, Mach Publ. Co. (1985).

*Primary Examiner*—Thurman K. Page
*Assistant Examiner*—Liliana Di Nola-Baron

(57) ABSTRACT

A simulated capsule-like medicament comprising a subcoating of a mixture of a water-soluble, film-forming polymer, e.g. hydroxypropylmethyl cellulose and a hydrophobic plasticizer, e.g. castor oil, which promotes a smooth uniform and substantially bubble free outer coating, e.g. gelatin, for the capsule-like medicament; capsule-like medicaments which are slightly bowed in shape; and a process of making such medicaments.

8 Claims, 2 Drawing Sheets

U.S. PATENT DOCUMENTS

| | | | |
|---|---|---|---|
| 3,573,966 | 4/1971 | Hostetler | 117/100 |
| 3,896,762 | 7/1975 | Banker | 118/30 |
| 4,222,166 | 9/1980 | Kurek et al. | 29/831 |
| 4,526,129 | 7/1985 | Braden | 118/503 |
| 4,669,416 | 6/1987 | Delgado et al. | 118/503 |
| 4,684,113 | 8/1987 | Douglas et al. | 269/21 |
| 4,797,287 | 1/1989 | Pich et al. | 424/464 |
| 4,816,259 | 3/1989 | Matthews et al. | 424/464 |
| 4,820,522 | 4/1989 | Radebaugh et al. | 424/468 |
| 4,820,524 | 4/1989 | Berta | 424/474 |
| 4,828,843 | 5/1989 | Pich et al. | 424/480 |
| 4,851,230 | 7/1989 | Tencza et al. | 424/467 |
| 4,867,983 | 9/1989 | Berta | 424/451 |
| 4,880,101 | 11/1989 | Wiggins | 198/403 |
| 4,921,108 | 5/1990 | Berta | 209/625 |
| 4,965,089 | 10/1990 | Sauter et al. | 427/3 |
| 4,966,771 | 10/1990 | Berta | 424/478 |
| 4,990,358 | 2/1991 | Berta | 427/3 |
| 5,032,074 | 7/1991 | Muto et al. | 425/272 |
| 5,054,258 | 10/1991 | Tait et al. | 53/137.2 |
| 5,146,730 | 9/1992 | Sadek et al. | 53/454 |
| 5,155,981 | 10/1992 | Tordini | 53/559 |
| 5,228,916 | 7/1993 | Berta | 118/30 |
| 5,234,099 | 8/1993 | Berta | 198/803.01 |
| 5,314,537 | 5/1994 | Berta | 118/30 |
| 5,391,230 | 2/1995 | Pastecki et al. | 118/503 |
| 5,436,026 | 7/1995 | Berta | 427/2.14 |
| 5,466,290 | 11/1995 | Berta | 118/20 |
| 5,498,441 | 3/1996 | Berta | 427/2.14 |
| 5,503,673 | 4/1996 | Berta | 118/16 |
| 5,514,216 | 5/1996 | Pastecki et al. | 118/503 |
| 5,607,044 | 3/1997 | Berta | 198/468.4 |
| 5,651,191 | 7/1997 | Walunas et al. | 34/236 |
| 6,120,801 * | 9/2000 | Parekh et al. | 424/463 |

FOREIGN PATENT DOCUMENTS

| | | | |
|---|---|---|---|
| 0 118 856 A1 | 9/1984 | (EP) | B07C/5/02 |
| 0 279 682 A3 | 8/1988 | (EP) . | |
| 0 319 318 | 6/1989 | (EP) . | |
| 0 194 502 B1 | 4/1990 | (EP) | G01N/33/52 |
| 0 246 693 A1 | 8/1992 | (EP) | A61K/9/48 |
| 2 588 888 | 4/1987 | (FR) | A61K/9/22 |
| 41-13997 | 8/1941 | (JP) . | |
| 142947 | 3/1969 | (NZ) . | |
| 214983 | 1/1986 | (NZ) . | |

* cited by examiner

SUBCOATED SIMULATED CAPSULE-LIKE MEDICAMENT

This invention is a divisional application of U.S. Ser. No. 09/389,793 filed Sep. 3, 1999, now U.S. Pat. No. 6,214,350 which is a divisional of U.S. Ser. No. 09/292,211 filed Apr. 15, 1999; U.S. Pat. No. 6,120,801 which is a divisional application of U.S. Ser. No. 08/802,185, filed Feb. 18, 1997, now U.S. Pat. No. 5,916,592; which is continuation of U.S. Ser. No. 07/784,623, filed Oct. 31, 1991, now U.S. Pat. No. 5,658,589, which is a continuation-in-part of U.S. Ser. No. 07/345,599 filed on Apr. 28, 1989, abandoned.

FIELD OF THE INVENTION

This invention relates to subcoated simulated capsule-like medicaments. More particularly this invention relates to a solid medicament caplet core which has been subcoated with a mixture of a water-soluble, film-forming polymer and a hydrophobic plasticizer and coated with a smooth outer coating to provide the appearance of a capsule-like medicament and a process of making such coated medicaments.

BACKGROUND OF THE INVENTION

Filled two-piece gelatin capsules for the encapsulation of various medicinal agents have been used for administering drugs since the mid-19th century. This capsule form of medicament proved to be very popular because hard gelatin capsules are tasteless, easily administered and easily filled either at a pharmacy or pre-filled in large quantities at commercial plants. While hard shell gelatin capsules are still popular dosage forms for pharmacist dispensed medicaments they have generally been discontinued in many over-the-counter products because of the risk of tampering with their contents.

Absent the susceptibility of capsule form medicaments to tamperings the capsule form was extremely popular with consumers because of a number of advantages. Many consumers prefer the gelatin form of capsule because of the perceived efficacy, taste, feel and swallowability of the gelatin capsule form of medicament.

This consumer preference for gelatin capsule-like medicaments provided a challenge to the industry to produce capsule-like medicaments which are tamper-proof yet provide the consumer with the advantages of a hard shell gelatin capsule-like dosage form. Norbert I. Berta developed simulated capsule-like medicaments and a process for making such capsule-like medicaments as disclosed in his U.S. Pat. No. 4,820,524. The entire disclosure of this issued U.S. patent is hereby incorporated herein by reference. Norbert I. Berta has also developed variations of the processes for making simulated capsule-like medicaments and apparatus for producing such medicaments as disclosed in U.S. Pat. No. 4,921,108 filed Dec. 4, 1987; U.S. Pat. No. 4,966,771 filed May 5, 1988; and U.S. Pat. No. 5,314,537 filed May 5, 1988. The simulated capsule-like medicaments developed by Berta were responsive to a long felt need in the industry to provide a simulated substitute for the popular dosage form of gelatin capsules. While gelatin coating of uncoated compressed medicaments such as acetaminophen is possible in accordance with the invention of Berta, it is difficult to control the quality of the surface appearance of such gelatin-coated caplets.

Beyond the development of a simulated capsule-like medicament several factors and considerations must be met to commercially produce a capsule which has a smooth, uniform and substantially bubble free outer coating appearance. A preferred gelatin-coated caplet is one in which two distinctly colored gelatin coating solutions are utilized to produce a bi-colored gelatin-coated caplet. The two overlapping distinctly colored gelatin coatings form a seam about the transverse axis of the medicament. The presence of this seam and the distinct bi-coloring contributes to the consumer's perception of these simulated capsule-like medicaments as equivalents to gelatin capsule dosage forms.

The gelatin coated caplet product must adequately simulate a capsule-like medicament from a consumer's sight and touch perspective and must therefore be absent of discoloration, pits and gouges. The presence of such physical imperfections may erode the consumer's perception as to the gelatin coated caplet's capsule-like nature and the tamper-free nature of this dosage form. Strong consumer confidence in the gelatin capsule-like nature and tamper-resistance of the simulated capsule medicament of the invention is of the utmost importance in the marketing of this dosage form and forms an object of the present invention. It is therefore an object of the present invention to provide a subcoating for a solid caplet medicament core which minimizes bubble formation, discoloration and other aesthetic imperfections to provide for a smooth, uniform and substantially bubble free outer coating appearance to simulated capsule-like medicaments.

SUMMARY OF THE INVENTION

The foregoing object of providing a simulated capsule-like medicament which has a smooth, uniform and substantially bubble free outer coating appearance has now been accomplished in accordance with the compositions and processes of the present invention.

In accordance with the purposes of the invention, as embodied and fully described herein, the invention comprises a simulated capsule-like medicament comprising: a solid caplet core comprising a medicament; a subcoating composition on the caplet core comprising a mixture of a water-soluble, film-forming polymer and a hydrophobic plasticizer; and a smooth outer coating whereby the subcoating composition promotes a smooth, uniform and substantially bubble free outer coating appearance to the capsule-like medicament.

In another embodiment of the present invention, there is provided a swallowable solid core having a smooth, uniform and substantially bubble free outer coating comprising a solid core containing a medicament which has an exterior surface that is coated with a subcoating composed of a mixture of a water-soluble, film-forming polymer selected from the group consisting of hydroxypropyl cellulose, hydroxypropylmethyl cellulose, mixtures of hydroxypropyl cellulose and hydroxypropylmethyl cellulose, mixtures of hydroxypropyl cellulose and methyl cellulose wherein the hydroxypropyl cellulose constitutes greater than 50 weight percent but less than 100 weight percent of the mixture of hydroxypropyl cellulose and methyl cellulose, mixtures of hydroxypropyl cellulose and hydroxyethyl cellulose wherein the hydroxypropyl cellulose constitutes greater than 80 weight percent but less than 100 weight percent of the mixture of hydroxypropyl cellulose and hydroxyethyl cellulose, mixtures of hydroxypropylmethyl cellulose and methyl cellulose wherein the hydroxypropylmethyl cellulose constitutes greater than 50 weight percent but less than 100 weight percent of the mixture of hydroxypropylmethyl cellulose and methyl cellulose, mixtures of hydroxypropylmethyl cellulose and hydroxyethyl cellulose wherein the hydroxypropylmethyl cellulose constitutes more than 80 weight percent but less than 100 weight percent of the mixture of hydroxypropylmethyl cellulose and hydroxyethyl cellulose and combinations of two or more thereof; and castor oil, wherein the subcoating provides an outer subsurface which is coated with a gelatinous coating, wherein the subcoating is provided in an amount which is effective to promote a smooth, uniform and substantially bubble-free outer coating appearance to capsule-like medicaments.

In preferred embodiments of the invention the water-soluble, film-forming polymer is hydroxypropylmethylcellulose, the hydrophobic plasticizer comprises castor oil and the smooth outer coating composition is gelatin. In more preferred embodiments, the hydroxypropylmethylcellulose and castor oil comprise from about 2 to about 8%, more preferably about 4 to about 6%, and most preferably about 4% by weight of the total weight of the subcoated caplet core.

In further preferred embodiments of the invention the medicament comprises a composition selected from the group consisting of acetaminophen, ibuprofen, loperamide, naproxen, pseudoephedrine, dextromethorphan, chlorphenarimine, and mixtures thereof.

In further preferred embodiments a solid caplet core of the capsule-like medicament has a slight convex bowed shape. Preferably, the bow represents an arcuate variance of about 1 to 5 degrees about a longitudinal axis of the caplet core.

As embodied and broadly described herein the invention further comprises a process for preparing a simulated capsule-like medicament comprising the steps of: compressing a mixture of a medicament and pharmaceutically acceptable excipients to form a solid caplet core; applying a subcoating composition comprising a mixture of a water-soluble, film-forming polymer and a hydrophobic plasticizer to the solid caplet core; and applying a smooth outer coating to the subcoated caplet core to provide a smooth, uniform and substantially bubble free outer coating appearance to the capsule-like medicament. The preferred components for the caplet core and the subcoating mixture are as described above. In preferred embodiments of the process of the invention the outer coating is gelatin and is applied at a temperature of from about 35 to 55° C., preferably at about 40 to 50° C.

DETAILED DESCRIPTION OF THE PREFERRED EMBODIMENTS OF THE INVENTION

Figure 1:
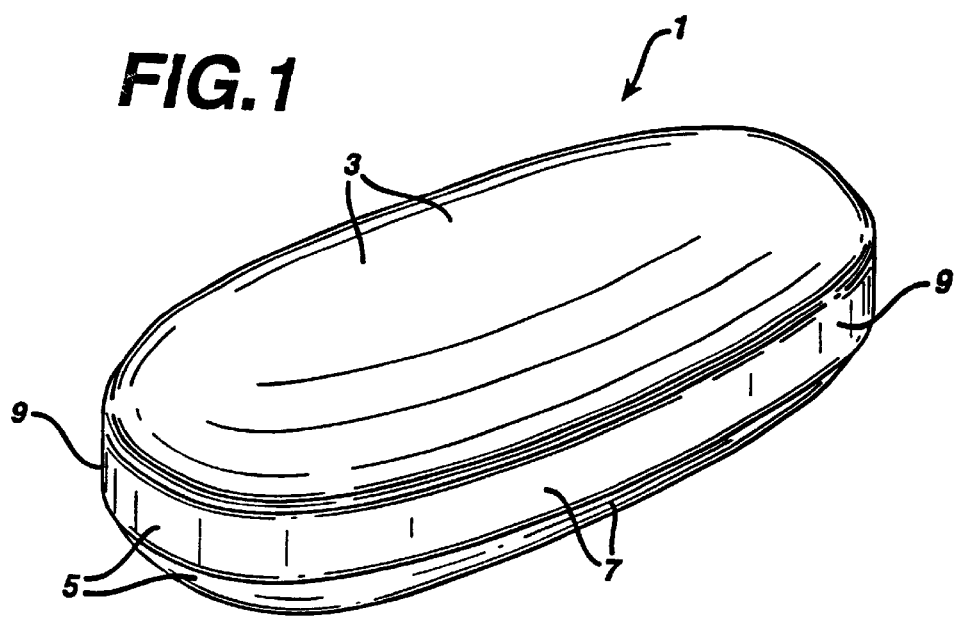
FIG. 1 is a front-top perspective view of a caplet core of the invention.

Reference will now be made in detail to preferred embodiments of the invention, examples of which are illustrated in the following examples section. The present invention provides a subcoating which is suitable for coating any swallowable solid core which will be subsequently coated with a gelatinous outer layer. The solid core may be of any shape which is suitable for the oral administration of drug substances including but not limited to tablet or capsule shapes. Suitable method of manufacturing solid cores are well known in the art such as the techniques on pages 1576–1607 of *Remington's Pharmaceutical Sciences*, Mack Publishing Company (Fifteenth edition), 1975 the text of which is hereby incorporated by reference. Currently the preferred solid core shapes for subcoating are solid core capsule-like shapes hereinafter referred to as caplets.

To achieve one of the object of the invention which is to provide a simulated capsule-like medicament which has a smooth, uniform and substantially bubble-free outer coating appearance, a subcoating is applied to the solid caplet medicament core to provide a compatible coating surface for the gelatinous coating. The subcoating composition in accordance with the invention provides a surface for gelatinous coating that minimizes bubble formation, discoloration and other aesthetic imperfections.

The capsule-like medicament of the invention comprises a solid caplet core of a medicament which can be compressed into a caplet core utilizing conventional excipients and tableting aids. Any pharmaceutical active or medicament that is capable of being formed into a caplet core, may be used in accordance with the invention. Examples of suitable medicaments which may be utilized in accordance with the invention include, but are not limited to, acetaminophen, ibuprofen, loperamide, naproxen, pseudoephedrine, dextromethorphan, chlorphenarimine, and mixtures thereof. These medicaments may be used alone or in combination such as a sinus headache combination comprising for example, acetaminophen and pseudoephedrine.

The subcoating composition of the present invention was developed to provide multiple functions required for a suitable subcoat. These functions and characteristics of the subcoat or pre-coat include the following: adequate film strength of the subcoating to allow the subcoated tablet to withstand mechanical transfer and maintain the integrity of the subcoat; compatibility of the subcoat material with the medicament to be coated; compatibility of the subcoat material with the smooth outer coating such that adequate pick-up of the smooth outer coating is achieved with a minimum of bubble formation on the final product; and compatibility of the subcoat material with the outer coating such that the subcoat does not adversely affect the color of the outer coating composition particularly where two distinct colors are utilized.

The subcoating composition of the invention also provides advantageous processing functions. The subcoating helps eliminate dust and other degradation of the medicament caplet core. The subcoating also prevents contamination of the gelatin coating solution by the medicament present by providing a full separation barrier between the gelatin coating solution and the medicament in the subcoated solid caplet core.

In accordance with the present invention, it was found that a subcoating composition which accomplishes the required functions comprises a mixture of a water-soluble, film-forming polymer and a hydrophobic plasticizer. One suitable group of water-soluble film-forming polymers are cellulose derivatives selected from the group consisting of hydroxypropylmethyl cellulose (hereinafter also referred to as HPMC) and hydroxypropyl cellulose (hereinafter also referred to as HPC) which may be used individually or combined in mixtures. Hydroxypropylmethyl cellulose and hydroxypropyl cellulose may also be combined with other cellulose derivatives such as methyl cellulose and hydroxyethyl cellulose. The amount of HPMC and/or HPC present in mixtures with methyl cellulose should be in the range of from about 50 weight percent to less than 100 weight percent of HPMC and/or HPC based on the dry weight of the components equalling 100 weight percent. The amount of HPMC and/or HPC present in mixtures with hydroxyethyl cellulose should be in the range of from about 80 mole percent to less than 100 weight percent of HPMC and/or HPC present in the mixture based on the dry weight of the components of the mixture equalling 100 weight percent. The molecular weight of the water-soluble film- forming polymers utilized in the present invention is not believed to be critical to the practice of the present invention. It is however recommended that the average molecular weight of the water-soluble film-forming polymer be in the range of from about 50,000 to 150,000. Suitable grades of hydroxypropylmethyl cellulose polymers within these weight ranges may be obtained from Dow Chemical Company designated as E50 and E150. Currently preferred water-soluble film forming polymers are hydroxypropylmethyl cellulose polymers having a molecular weight of about 50,000. The degree of substitution of the cellulose derivative utilized in the subcoating should conform to the degree of substitution approved for this use by the FDA. For example the degree of substitution of HPMC should be in the range of from 19–30 percent methoxyl substitution and from 4–12 percent propyl substitution and preferably in the range of from 28–30 methoxyl percent and 7–12 percent propyl. Methyl cellulose should be substituted in the range of from 27.5–31.5 percent methoxy groups. The currently preferred hydrophobic plasticizer is castor oil. The amount of subcoating composition utilized should be an amount effective to provide the above-mentioned desirable functions and characteristics of the subcoated caplet core.

Optimization of the coating amount will vary in accordance with the size of the caplet core and particular medicaments utilized. Preferably, a mixture of the water-soluble film forming polymer (for example the preferred hydroxypropylmethyl cellulose) and castor oil comprises from about 2 to about 8%, more preferably about 4 to about 6% and most preferably about 4% by weight of the total weight of the subcoated caplet core. The amount of castor oil present as a hydrophobic plasticizer comprises from about 0.1 to about 1% by weight of the total weight of the subcoated caplet core. Preferably the amount of water-soluble film-forming polymer e.g. hydroxypropylmethyl cellulose, to the hydrophobic plasticizer e.g. castor oil, is on the order of about 20:1.

It is important that the outer coating of the simulated capsule-like medicament be smooth, uniform and substantially bubble free to provide the perception of a capsule-like medicament. To achieve superior simulation of gelatin capsule dosage forms it is preferred to use a dual color outer coating which meets at a distinct seam at about the middle of the coated medicament caplet. The preferred outer coating composition is gelatin whereby the subcoated caplet core is dipped into a gelatinous solution. More preferably opposite ends of a subcoated medicament caplet core are dipped into two gelatinous solutions of distinct color to produce a dual colored capsule-like medicament. The amount of gelatinous coating added to the product is dependent upon the outer appearance desired for the product. Generally, enough gelatinous coating must be added on to the caplet to provide a smooth uniform and bubble free outer coating appearance and provide a gelatinous feel to the touch and in the mouth of consumers swallowing the simulated capsule-like medicament. A preferred gelatinous coating add-on is about 6.0 to about 8.3% by weight of the total weight of the simulated capsule-like medicament.

It is also recommended that the gelatin coating utilized in the present invention for coating the caplet surface be provided in an aqueous solution having a gelatin concentration of from in the range of about 20 weight percent to about 40 weight percent gelatin. The apparent viscosity of this gelatin solution is recommended to be in the range of from about 800 to about 1000 cps as measured at about 40° C.–50° C. temperature on a Brookfield viscometer. The preferred gelatin for the practice of the present invention is a mixture of in the range of from about 60 weight percent to about 80 weight percent of bone gelatin and in the range of about 40 weight percent to about 20 weight percent of pork gelatin on a dry weight basis with the total weight percent of the dry components totalling 100 weight percent. The currently preferred gelatin mixture is 70 weight percent bone gelatin and 30 weight percent pork gelatin.

Figure 3:
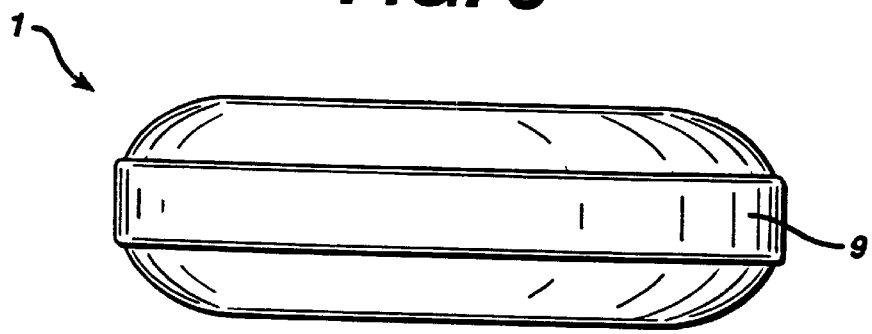
FIG. 3 is a side elevational view of the caplet core.
Figure 4:
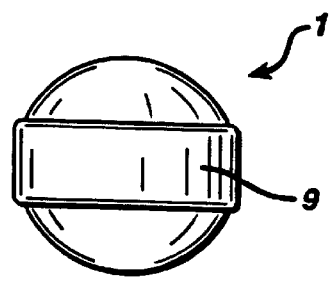
FIG. 4 is a front elevational view of the caplet core.
Figure 5:
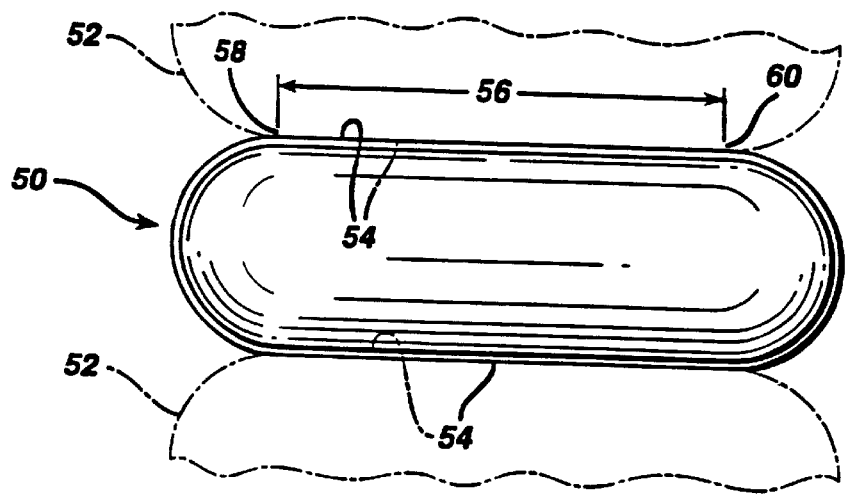
FIG. 5 is a top plan view of a caplet of the prior art.

In preferred embodiments the capsule-like medicament of the invention has a caplet core which has a slight convex bowed shape. This shape is illustrated in FIGS. 1–4 herein which are described in more detail below. This bowed shape serves two important functions. It was found that caplets of the prior art that were unbowed or had straight edges were more prone to stick to each other and form "twins." Formation of twins or twinning is the joining of one or more caplets together during processing along edges in contact with each other. Further, caplets with straight edges also tend to stick or twin together temporarily and cause surface imperfections, e.g. pitting and/or gouging. Twinning of straight edged prior art caplets is illustrated in FIG. 5 herein, which is described in more detail below.

Twinning of caplets can apply to any situation where the caplet cores have a tacky or sticky outer coating due to the nature of the ingredients comprising the medicament or those comprising the subcoating or gelatinous outer coating of the caplets. For example, coatings such as shellac, seal coatings, or sugar coatings also provide tacky caplets which are prone to form twins. It is therefore advantageous in preparing simulated capsule-like medicaments in accordance with the present invention, as well as, the handling of all tacky caplet cores to utilize caplets which have a slight bowed shape which reduces twinning of caplets due to contact during processing. The bowed shape minimizes the point of contact between caplets and thus reduces sticking or twinning of caplets to each other.

In preferred embodiments of the present invention, the bowing is a convex bow that stems from the middle of a longitudinal axis of the caplet core outwards toward the two ends. The bowed variance along the longitudinal axis of the caplet core is on the order of about 1 to 5 degrees. This arcuate variance is great enough to reduce the twinning of the caplets during processing without detracting from the capsule-like shape and appearance of the final medicament product which is important to its simulation of a gelatin capsule.

Another surprising advantage of providing caplets with a slightly convex bowed shape is that the shape provides an increase in tablet hardness of up to about 10% as compared with regular unbowed caplet shaped cores. The increase in hardness may be due to some degree to the increased thickness of the caplet about the center area but the magnitude of increase achieved could not be anticipated by this slight change in thickness at this area. It has also been found advantageous to provide a convex bow shaped caplet since the increased hardness contributes to preventing surface pitting and breaking of the cores during the coating process.

Figure 2:
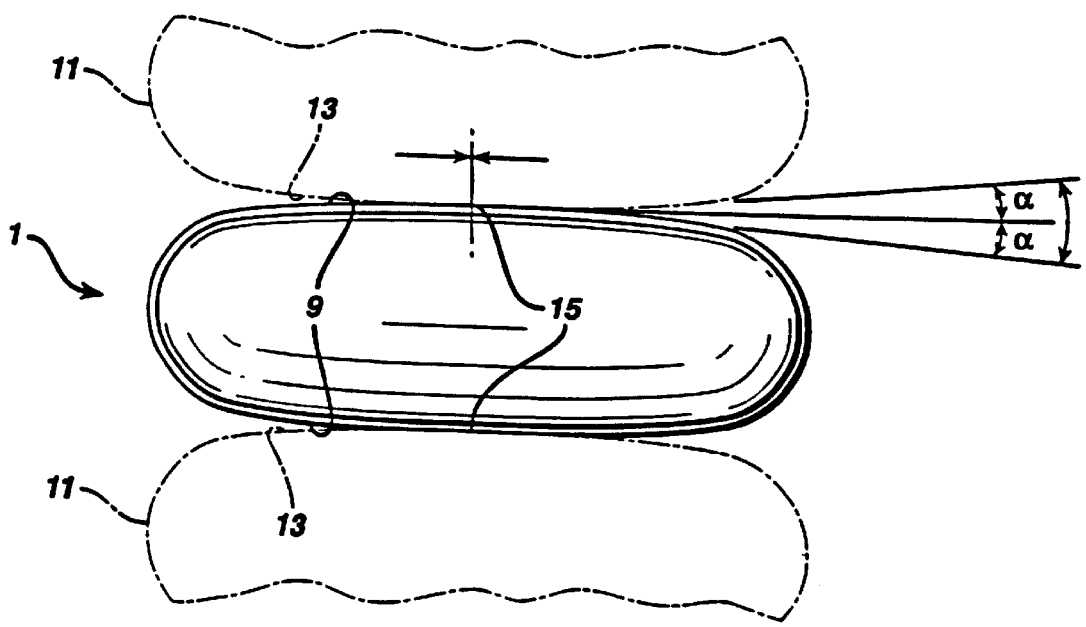
FIG. 2 is a top plan view of the caplet core.

The bow shaped caplet core of the invention will now be described with reference to the Figures herein. FIG. 1 is a perspective view of a caplet core (1) from the top (3), front (5) and right (7) sides. A peripheral edge surface or "belly band" (9) extends longitudinally around the side of the caplet core (1). FIG. 2 shows a top plan view of the caplet core (1) with adjacent caplet cores (11) shown in broken lines on either side of the caplet core (1) at their belly bands (9) and (13). In accordance with the slight bowed shape of the belly bands (9) and (13) the adjacent caplet cores have only a single point of contact (15) with each other along the arcuate edge surface of the belly band. The amount of bowing need only be slight, on the order of 1 to 5 degrees as is illustrated by angle V in the drawing. FIG. 3 is a side elevational view of the caplet core (1) and belly band (9). FIG. 4 is a front elevational view of the caplet core (1) and belly band (9).

FIG. 5 is a view similar to FIG. 2 showing a straight edged or unbowed caplet core (50) of the prior art with adjacent or twinned caplet cores (52) in contact therewith along straight edged belly bands (54) with a point of contact along the entire straight edge of the caplet core as illustrated by the dimension (56) marked out by length indicators (58) and (60). This large potential area of contact along the entire straight edge (56) of caplet cores of the prior art encourages sticking or twinning of caplets to each other and production of surface imperfect or twinned caplets which are not suitable for further commercial use as simulated capsule-like medicaments.

In accordance with the present invention, a process is also provided for preparing simulated capsule-like medicaments. The process comprises the steps of compressing a mixture of medicament and compatible excipients to form a solid caplet core. The excipients chosen and the compression applied should be adequate to provide a caplet with sufficient hardness for prevention of surface pitting and caplet breakage during coating of the caplet core. For capsule-like acetaminophen medicaments the preferred hardness is about 10–14 Kp and more preferably about 10–11 Kp.

To provide a capsule shape appearance the width to thickness ratio about the simulated capsule-like medicament should be as close as possible to one. Gelatin capsule dosage forms are generally round in shape and therefore have a width to thickness ratio by definition of one. A preferred tooling dimension which gives this appearance is 0.750 inches by 0.250 inches by 0.075 inches. The thickness resulting from this tooling is 0.244 inches. These dimensions may vary as the size of the caplet varies but efforts should be made to keep the width to thickness ratios as close as possible to one to provide adequate simulation of a gelatin capsule dosage form.

The subcoating composition, preferably a mixture of hydroxypropylmethyl cellulose and castor oil, is applied from an 8% weight by weight aqueous solution. Acceptable subcoatings can be applied with subcoating solutions of from 6 to 8% concentration but 8% is preferred since a shorter amount of spraying time is required to provide the desired amount of subcoating on the caplet core. Coating levels above 8% were found to provide less desirable subcoatings because of unevenness of application of the subcoating composition. The concentration of the subcoating solution is not considered critical to the coating process. The caplet cores are subcoated to preferably provide about 2 to 8%, more preferably about 4 to 6 and most preferably about 4% subcoating by weight of the total weight of the subcoated caplet core.

A smooth outer coating is applied to the subcoated caplet core to provide a smooth, uniform and substantially bubble free outer coating appearance to the capsule-like medicament. The preferred outer coating is a gelatin outer coating and more preferably a bicolor gelatin coating. Application of the gelatinous coating is by dipping of the subcoated caplet core into a gelatin solution which has a temperature in the range of about 35–55° C., preferably about 40 to 50° C. Higher gelatin solution temperatures generally result in a lower viscosity of the gelatin solution. The gelatin solution temperature is varied to adjust the viscosity and gelatin pick-up on the subcoated caplet.

Gelatin dipping may be performed by any adequate means including hand dipping of the caplets into a gelatin solution. A particularly preferred method is performed in accordance with the teachings of Berta in the aforementioned U.S. Pat. No. 4,820,524 which has been incorporated herein by reference. This patent provides a useful process for providing bi-color gelatin coated capsule-like medicaments which have a slightly raised seam about the color overlapping portion of the caplet which contributes to its simulated capsule-like feel and appearance. Any color gelatin solutions may be utilized, but it is preferred that the colors be distinct.

EXAMPLE

The invention will now be illustrated by example. The example is not intended to be limiting of the scope of the present invention but read in conjunction with the detailed and general description above provide further understanding of the present invention and an outline of a process for preparing the compositions of the invention.

Example 1

Simulated Capsule-like Acetaminophen Dosage Form

An acetaminophen caplet core was prepared from the following components:

|     |                              | Mg/Caplet |
| --- | ---------------------------- | --------- |
| I.  | Active and Excipients        |           |
|     | acetaminophen, USP           | 500.0 mg  |
|     | powdered cellulose, NF       | 40.0 mg   |
|     | pregelatinized starch, NF    | 10.0 mg   |
|     | sodium starch glycolate, NF  | 10.0 mg   |
| II. | Granulating Agent            |           |
|     | starch, NF                   | 40.0 mg   |
|     | purified water, USP          | q.s.      |
| III | Dry Adds                     |           |
|     | magnesium stearate, NF       | 3.20 mg   |
|     | Total                        | 603.2 mg  |

Working Directions

A. Weigh the desired components of Part I in the proportions provided and add them to a bowl of a fluid bed granulator such as an AEROMATIC brand granulator.

B. Prepare the granulating agent (Part II) by adding the purified water to a processing tank with approximately 15 grams of water for each gram of starch NF. Slowly mix in the starch and heat the mixture until the temperature reaches about 82–84° C.

C. With the components of Part I in a heated fluidized state and an inlet air temperature of 75–85° C., spray the granulating agent onto the powders.

D. After all the granulating agent has been sprayed, dry the granulated powders to a moisture content of about 1.4 to 1.9% as determined by loss on drying using for example a COMPUTRAC brand analyzer.

E. Sieve the dried granulation, for example, using a GLATT QUICK brand sieve stator No. 3, screen No. 1.5 mm, 1,000 RPM.

F. Blend the sieved and dried granulation with the powders of Part III using a suitable mixer such as a twin shell, ribbon or planetary mixer.

G. Load the granulation into a tableting machine and compress the caplets using a capsule-shaped tooling device of the dimensions 0.750"×0.250"×0.075". The thickness resulting from this tooling is 0.244". Ideal caplet hardness is about 10 Kp.

H. Coat the compressed solid caplet cores of step G by spraying with an 8% aqueous solution which comprises a mixture of hydroxypropylmethyl cellulose and castor oil in a ratio of about 20:1 (this mixture is commercially available from Colorcon as Opadry YS-5-7042). The subcoating solution is applied utilizing a Accla-Cota perforated pan coating unit manufactured by Thomas Engineering (Hoffman Estates, Ill.) to achieve a 4% subcoating by weight of the total weight of the subcoated caplet core.

Gelatin Dipping

The subcoated caplet core is then subjected to gelatin dipping. The gelatin used is preferred to be a mixture of 70 weight percent bone and 30 weight percent pork gelatin which may be obtained separately from Kind and Knox. The gelatin solution for dipping was a 30 weight percent aqueous solution with an apparent viscosity of about 800–1,000 cps as measured at 40° C. by a Brookfield viscometer. The gelatin dipping may be accomplished by hand e.g. by dipping half of the subcoated caplet core into a yellow gelatin solution at about 40° C. for about 6 seconds and withdrawing the half coated caplet and allowing it to dry before dipping the as yet non-gelatin coated half of the caplet into a red gelatin solution at a temperature of 40° C. for about 6 seconds. Whereby a slight overlapping of the two distinctly colored gelatinous cores is achieved about the midway portion of the caplet.

The caplet may also be gel dipped in accordance with the process and apparatus as described in U.S. Pat. No. 4,820,524 of Berta which has been incorporated herein by reference.

The scope of the present invention is not limited by the description, examples and suggested uses herein and modifications can be made without departing from the spirit of the invention. For example, other components may be added to the caplet core including various flavorings, preservatives and other pharmaceutical excipients. The present invention may also be provided in a sustained release formulation wherein the caplet core comprises a medicament and sustained release promoting excipients. The simulated capsule-like compositions and slightly bowed caplets may also be applicable to non-medicinal applications such as oral dosage forms of vitamins and/or other nutrients.

Application of the compositions and processes of the present invention for medical and pharmaceutical uses can be accomplished by clinical, medical and pharmaceutical methods and techniques as are presently or prospectively known to those skilled in the art. Thus it is intended that the present invention cover the modifications and variations of this invention provided that they come within the scope of the appended claims and their equivalents.

What is claimed is:

1. A caplet comprising a caplet core containing a pharmaceutical active, said core having longitudinal sides and said sides having a peripheral edge surface that is bowed in shape, wherein said caplet is coated in a gelatinous material.

2. The caplet of claim 1 wherein the bowed shape is convex and represents a variance of about 1 to about 5 degrees about a longitudinal axis of the caplet core.

3. The caplet of claim 2 which also contains a subcoat.

4. The caplet of claim 3 wherein the subcoat comprises a water-soluble film-forming polymer.

5. The caplet of claim 4 wherein the water-soluble film-forming material is hydroxypropylmethylcellulose.

6. A caplet comprising a caplet core containing a pharmaceutical active, said core having longitudinal sides and said sides having a peripheral edge surface that is bowed in shape, said bow shape is convex and represents a variance of about 1 to about 5 degrees about a longitudinal axis of the caplet core, wherein the caplet core is coated in a gelatin solution, and a subcoat is provided between the caplet core and the gelatin.

7. The caplet of claim 6 wherein the subcoat comprises a water-soluble film-forming polymer.

8. The caplet of claim 7 wherein the water-soluble film-forming polymer is hydroxypropylmethylcellulose.

* * * * *